United States Patent
Cabri et al.

(10) Patent No.: US 6,642,378 B1
(45) Date of Patent: Nov. 4, 2003

(54) PROCESS FOR THE SYNTHESIS OF BETA-LACTAM DERIVATIVES

(75) Inventors: Walter Cabri, Rodano (IT); Enrico Siviero, Rodano (IT); Paola Luigia Daverio, Rodano (IT); Tania Cristiano, Rodano (IT); Claudio Felisi, Rodano (IT); Davide Longoni, Rodano (IT)

(73) Assignee: Antibioticos S.p.A. (IT)

( * ) Notice: Subject to any disclaimer, the term of this patent is extended or adjusted under 35 U.S.C. 154(b) by 0 days.

(21) Appl. No.: 10/031,990

(22) PCT Filed: Jul. 24, 2000

(86) PCT No.: PCT/EP00/07068

§ 371 (c)(1),
(2), (4) Date: Mar. 13, 2002

(87) PCT Pub. No.: WO01/07443

PCT Pub. Date: Feb. 1, 2001

(30) Foreign Application Priority Data

Jul. 27, 1999 (IT) .......................................... MI99A1655

(51) Int. Cl.⁷ ............................................. C07D 501/04
(52) U.S. Cl. ....................................................... 540/222
(58) Field of Search ......................................... 540/222

(56) References Cited

U.S. PATENT DOCUMENTS

| 3,966,717 A | | 6/1976 | Cook et al. |
| 5,453,535 A | * | 9/1995 | Fischer ........................ 560/156 |

FOREIGN PATENT DOCUMENTS

| GB | 2018764 A | 10/1979 |
| GB | 2218093 A | 11/1989 |

* cited by examiner

*Primary Examiner*—Mark L. Berch
(74) *Attorney, Agent, or Firm*—Rothwell, Figg, Ernst & Manbeck, p.c.

(57) ABSTRACT

The invention is directed towards a process for the preparation of Cefuroxime acid or for a corresponding pharmaceutically acceptable salt or ester. The process comprises the carbamoylation of a Cefuroxime precursor with an activated isocyanate. Additionally, the process is characterized by the fact that a carbonic $C_1$–$C_4$ alkyl ester is used as a solvent for the carbamoylation reaction.

8 Claims, No Drawings

PROCESS FOR THE SYNTHESIS OF BETA-LACTAM DERIVATIVES

The invention relates to a process for the synthesis of Cefuroxime acid (I), i.e. (6R, 7R)-7-[[2-furanyl (sin-methoxyimino)acetyl]amino]-3-carbamoyloxymethylceph-3-em-4-carboxylic) acid, and the salts thereof, starting from 3-hydroxymethylceph-3-em precursors with activated isocyanates in carbonic acid esters.

Cefuroxime is a cephalosporin widely used in the treatment of bacterial infections thanks to its effective, broad spectrum antibacterial activity against gram-negative bacterials, in particular in the treatment of immunodepressed patients.

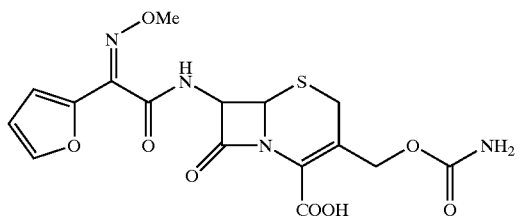

The acid product is the precursor both of the corresponding sodium salt, for the injection administration, and of the corresponding 1-acetyloxy ester (Cefuroxime axetil), for the oral administration.

Said molecules are valuable in that they are highly resistant to β-lactamases due to the methoxyimino group present in the side chain at the 7- position of the cephalosporanic ring.

As far as the carbamoylation step of the 3-hydroxymethylceph-3-em precursors is concerned, the known synthetic routes for the preparation of Cefuroxime make use of solvents, which involves potential risks connected with their inflammability and toxicity. The method disclosed in U.S. Pat. No. 3,966,717 comprises the conversion of diphenylmethyl-3-hydroxymethyl-7β-(thien-2-yl) acetamidoceph-3-em-4-carboxylate into the corresponding 3-carbamoyloxymethyl derivative by reaction with trichloroacetylisocyanate in acetone and subsequent hydrolysis.

On the other hand, the synthesis disclosed in U.S. Pat. No. 4,284,767 comprises the reaction of (6R,7R)-7-[[2-furanyl (sin-methoxyimino)acetyl]amino]-3-hydroxymethylceph-3-em-4-carboxylic acid with dichlorophosphinylisocyanate in tetrahydrofuran and the subsequent recovery of the product in the form of the sodium salt.

Finally the synthesis described in U.S. Pat. No. 4,775,750 comprises the conversion of the same intermediate by reaction in methyl or ethyl acetate with chlorosulfonyl isocyanate.

It has now surprisingly been found that Cefuroxime 3-hydroxymethyl precursors can be carbamoylated by reaction with activated isocyanates, using carbonic acid $C_1$–$C_4$ esters, preferably dimethylcarbonate and diethylcarbonate, as reaction solvents. The risks involved by the use of said solvents are remarkably lower than those connected with the use of the solvents cited above. Furthermore, said alkyl carbonates have remarkably lower toxicity than the solvents reported above, THF, alkyl acetates and acetone.

It should be pointed out that said reaction with isocyanates, which are extremely aggressive reactants, in solvents such as alkyl carbonates, has never before been reported in literature.

In the following table, the various solvents cited above are compared. The reported data are those of the respective safety requirements reported on MSDS (Material Safety Data Sheet)—OHS.

TABLE

|  | Flash point (° C.) | oral DL50 rat (mg/Kg) |
|---|---|---|
| Acetone | −18.0 | 5800 |
| Tetrahydrofuran | −17.2 | 2816 |
| Methyl acetate | −10.0 | 5480 |
| Ethyl acetate | −4.0 | 5620 |
| Dimethylcarbonate | 21.7 | 13000 |
| Diethylcarbonate | 33.0 | 15000 |

It is clear that the use of carbonic acid esters, in particular dimethyl or diethyl carbonate, involves much lower potential risks than those expected when using the solvents cited in the prior art patents.

The present invention provides remarkable advantages in the industrial processes for the production of Cefuroxime. In fact, the method of the invention provides good quality Cefuroxime acid in yields quite comparable with those expected with the prior art methods.

Moreover, the acid product can easily be converted into the corresponding pharmaceutically acceptable salt or ester, preferably into Cefuroxime sodium salt and Cefuroxime axetil, by using conventional techniques known to those skilled in the art.

The process of the present invention comprises the conversion of a Cefuroxime 3-hydroxymethyl or 3-hydroxymethyl-ceph-3-em precursor into the corresponding 3-carbamoyloxymethyl derivative by reaction in a solution of the precursor at a concentration ranging from 1 to 20% by weight, with an activated isocyanate/precursor molar ratio ranging from 1 to 5, wherein the activated isocyanate is preferably chlorosulfonyl isocyanate, using as solvent a carbonic acid $C_1$–$C_4$ alkyl ester, preferably dimethylcarbonate, at temperatures from −40 to 20° C., preferably from 0 to 10° C.

The progress of the carbamoylation reaction is monitored by HPLC chromatography. The reaction is over in 15÷60 minutes, when the substrate content in the final mixture decreases below 2% of the starting amount.

The reaction is then quenched by addition of water or, preferably, of an acidic aqueous solution, preferably an aqueous hydrochloric acid solution.

The product can be optionally filtered or, alternatively, recovered as the sodium salt as described in U.S. Pat. No. 4,775,750.

The following examples illustrate the process of the invention in greater detail.

The substrate used in the tests described in the following examples was prepared according to the procedure described by Wilson E. M. (Chemistry and Industry 1984, 217).

EXAMPLE 1

A 1:1 solution of chlorosulfonyl isocyanate (2.4 ml) in dimethylcarbonate was dropped into a suspension of (6R, 7R)-7-[[2-furanyl(sin-methoxyimino)acetyl]amino]-3-hydroxymethyl-ceph-3-em-4-carboxylic acid (3.6 g) in dimethylcarbonate (35 ml) cooled to 0–4° C., under inert atmosphere, keeping the temperature below 5° C.

When the addition of the reactive was completed, the mixture was kept at 0÷5° C. until the starting substrate was completely converted.

18% Hydrochloric acid (35 ml) was then added, keeping the heterogeneous mixture at a temperature ranging from 10 to 15° C. until the synthesis intermediate was completely hydrolysed.

Cefuroxime acid was recovered by filtration in the form of a white crystalline powder (3.8 g) in a 95% yield, or Cefuroxime sodium salt was recovered by the method described in U.S. Pat. No. 4,775,750 in similar yields.

The recovered product had high HPLC purity (>95%), and was characterized by $^1$H-NMR, $^{13}$C-NMR and mass spectroscopies, which gave the same data as those reported in literature for Cefuroxime.

EXAMPLE 2

A 1:1 solution of chlorosulfonyl isocyanate (1.9 ml) in diethylcarbonate was dropped into a suspension of (6R,7R)-7-[[2-furanyl(sin-methoxyimino)acetyl]amino]-3-hydroxymethyl-ceph-3-em-4-carboxylic acid (3.1 g) in diethylcarbonate (35 ml), cooled at 0° C. under inert atmosphere, until complete dissolution of the solid in solution.

When the addition of the reactive was completed, the mixture was kept at 0÷5° C. for 30', then a 18% hydrochloric acid solution (35 ml) was added thereto.

After 90' at temperatures ranging from 10 to 15° C., the thick white mixture was filtered to recover Cefuroxime acid (3.1 g) in a 90% final yield.

The NMR and Mass spectroscopical characterizations proved that the recovered product and that obtained in example 1 were identical.

EXAMPLE 3

A 1:1 solution of trichloroacetyl isocyanate (4.2 ml) in dimethylcarbonate was dropped into a suspension of (6R,7R)-7-[[2-furanyl(sin-methoxyimino)acetyl]amino]-3-hydroxymethyl-ceph-3-em-4-carboxylic acid (4.5 g) in dimethylcarbonate (45 ml) cooled to 0÷4° C., under inert atmosphere, keeping the temperature below 5° C.

When the addition of the reactive was completed, the mixture was kept at 0÷50C. until the starting substrate was completely converted.

Following the procedure described in U.S. Pat. No. 3,966,717, Cefuroxime sodium salt was recovered in 75% yields.

In this case also, the recovered product was characterized by $^1$H-NMR, $^{13}$C-NMR and mass spectroscopies, obtaining the same data as those reported in literature for Cefuroxime.

EXAMPLE 4

A 1:1 solution of dichlorophosphinyl isocyanate (2.5 ml) (prepared with the method described in U.S. Pat. No. 3,314,848) in diethylcarbonate was dropped into a suspension of (6R,7R)-7-[[2-furanyl(sin-methoxyimino)acetyl]amino]-3-hydroxymethyl-ceph-3-em-4-carboxylic acid (6.7 g) in diethylcarbonate (80 ml), cooled to 0÷4° C., under inert atmosphere, keeping temperature below 5° C.

When the addition of the reactive was completed, the mixture was kept at 0÷5° C. until the starting substrate was completely converted.

Following the procedure described in U.S. Pat. No. 4,284,767, Cefuroxime acid was recovered in 70% yields.

In this case also, the recovered product was characterized by $^1$H-NMR, $^{13}$C-NMR and mass spectroscopies, obtaining the same data as those reported in literature for Cefuroxime.

What is claimed is:

1. A process for the preparation of Cefuroxime acid or a corresponding pharmaceutically acceptable salt or ester which comprises the carbamoylation of (6R,7R)-7-[[2-furanyl(sin-methoxyimino)acetyl]amino]-3-hydroxymethylceph-3-em-4-carboxylic acid with an activated isocyanate, in the presence of a carbonic acid $C_1$–$C_4$ alkyl ester as solvent for said carbamoylation reaction, and the optional formation of the salt or ester from Cefuroxime acid.

2. A process as claimed in claim 1, in which said reaction solvent is dimethylcarbonate.

3. A process as claimed in claim 1, in which the activated isocyanate is chlorosulfonyl isocyanate.

4. A process according to claim 1, in which the (6R,7R)-7-[[2-furanyl(sin-methoxyimino)acetyl]amino]-3-hydroxymethylceph-3-em-4-carboxylic acid is present at a concentration ranging from 1 to 20% by weight and is reacted with activated isocyanate in an activated isocyanate/precursor molar ratio ranging from 1 to 5, at temperatures from −40° C. to 20° C.

5. A process according to claim 1, in which the carbamoylation reaction is quenched by addition of water or an acidic aqueous solution.

6. A process as claimed in claim 5, in which said acidic aqueous solution is a hydrochloric acid solution.

7. A process as claimed in claim 1, in which the product is recovered as the sodium salt.

8. A process according to claim 4, wherein the temperature is between 0° to 10° C.

\* \* \* \* \*